(12) United States Patent
Yamabe

(10) Patent No.: US 9,158,104 B2
(45) Date of Patent: Oct. 13, 2015

(54) OPTICAL COUPLER DEVICE AND CONFOCAL OBSERVATION SYSTEM

(71) Applicant: HOYA CORPORATION, Tokyo (JP)

(72) Inventor: Toshiaki Yamabe, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 0 days.

(21) Appl. No.: 14/404,526

(22) PCT Filed: May 7, 2013

(86) PCT No.: PCT/JP2013/062854
§ 371 (c)(1),
(2) Date: Nov. 28, 2014

(87) PCT Pub. No.: WO2013/179860
PCT Pub. Date: Dec. 5, 2013

(65) Prior Publication Data
US 2015/0144805 A1 May 28, 2015

(30) Foreign Application Priority Data
May 29, 2012 (JP) .................................. 2012-122179

(51) Int. Cl.
*G01N 21/64* (2006.01)
*G02B 23/24* (2006.01)
(Continued)

(52) U.S. Cl.
CPC .............. *G02B 23/2469* (2013.01); *A61B 1/00* (2013.01);
(Continued)

(58) Field of Classification Search
CPC ... H04J 14/02; H04J 14/0283; H04J 14/0209; H04J 14/0286; H04J 14/0279; G01N 2021/6484; G01N 21/64; G01N 2201/08
See application file for complete search history.

(56) References Cited

U.S. PATENT DOCUMENTS 4,552,165 A 11/1985 Luska
5,953,470 A * 9/1999 Toyohara ........................ 385/24
(Continued)

FOREIGN PATENT DOCUMENTS

JP 61-038907 2/1986
JP 2004-061982 2/2004
(Continued)

OTHER PUBLICATIONS

Search report from PCT/JP2013/062854, mail date is Jun. 25, 2013.

*Primary Examiner* — Kiho Kim
(74) *Attorney, Agent, or Firm* — Greenblum & Bernstein P.L.C.

(57) ABSTRACT

A fourth port of a first WDM-type optical coupler and a fifth port of a second WDM-type optical coupler are optically connected, and a second port of the first WDM-type optical coupler and an eighth port of the second WDM-type optical coupler are optically connected. A light source for emitting excitation light is connected to a first port of the first WDM-type optical coupler, and a light-receiving section (light detector) is connected to a sixth port of the second WDM-type optical coupler. Excitation light is emitted through a seventh port of the second WDM-type optical coupler toward an observed subject, fluorescence from the observed subject is acquired through the seventh port of the second WDM-type optical coupler, and input fluorescence is detected by the light-receiving section.

14 Claims, 9 Drawing Sheets

(51) Int. Cl.
- *G02B 23/26* (2006.01)
- *A61B 1/00* (2006.01)
- *A61B 1/04* (2006.01)
- *A61B 1/06* (2006.01)
- *G02B 21/00* (2006.01)
- *G02B 6/12* (2006.01)
- *G02B 6/293* (2006.01)

(52) U.S. Cl.
CPC ........ *A61B 1/00163* (2013.01); *A61B 1/00172* (2013.01); *A61B 1/043* (2013.01); *A61B 1/063* (2013.01); *G01N 21/64* (2013.01); *G01N 21/645* (2013.01); *G02B 6/12* (2013.01); *G02B 6/293* (2013.01); *G02B 6/2938* (2013.01); *G02B 21/0028* (2013.01); *G02B 21/0076* (2013.01); *G02B 23/26* (2013.01); *G01N 2021/6417* (2013.01); *G01N 2021/6484* (2013.01); *G01N 2201/06113* (2013.01); *G01N 2201/08* (2013.01)

(56) References Cited

U.S. PATENT DOCUMENTS 6,160,627 A * 12/2000 Ahn et al. ................. 356/477
2006/0056784 A1    3/2006 Hauger et al.

FOREIGN PATENT DOCUMENTS

JP    2006-510932    3/2006
JP    2010-262149    11/2010

* cited by examiner

OPTICAL COUPLER DEVICE AND CONFOCAL OBSERVATION SYSTEM

TECHNICAL FIELD

The present invention relates to an optical coupler device which uses optical couplers, and particularly relates to a confocal observation system which uses this optical coupler device.

BACKGROUND ART

As a passive optical device which branches and combines light, an optical coupler (optical fiber coupler) is used. An optical coupler is utilized not only for fiber-optic communication, but also in a confocal endoscope system, etc., in recent years. For example, as a confocal endoscope system which uses excitation light, a configuration using a 2×2 WDM (wavelength division multiplexing) type optical coupler is provided with a first port and second port on the input side (output side) and a third port and fourth port on the output side (input side) is known (PLT 1). In this confocal endoscope system, the excitation light, which is emitted from the laser light source, enters the first port and is emitted from the third port. The fluorescence of the subject due to the emitted excitation light enters the third port and is guided through the second port to a light-receiving section. Further, this optical coupler ideally is designed so that excitation light with a wavelength of 488 nm enters from the first port and branches out to the third port and fourth port at a 90:10 ratio, while fluorescent light with a peak wavelength of 515 nm enters from the third port and branches out to the first port and second port at a 0:100 ratio.

CITATIONS LIST

Patent Literature

PLT 1: Japanese Unexamined Patent Publication No. 2010-262149A

SUMMARY OF INVENTION

Technical Problem

In a 2×2 WDM-type optical coupler, the transmittance of light that enters from one input side port and exits from the output side port changes sinusoidally with respect to the wavelength, and is complementary (180 degrees out of phase) at the straight ports and the cross ports. Therefore, to efficiently guide the excitation light to the scanning fiber side and have the fluorescence mainly branched to the light-receiving section side, the peak of transmittance to one port has to be matched with the wavelength of the excitation light as much as possible (substantially single wavelength), while the peak of transmittance to the other port has to be matched with the peak wavelength of the fluorescence. However, the spectrum of the fluorescence is generally broader than the difference between the wavelength of excitation light and the peak wavelength of fluorescence, so most of the fluorescence with wavelengths near the edges of the spectrum ends up being branched to the first port side to which the laser light source is connected.

That is, in a scanning (single fiber) endoscope (SFE) using a confocal system according to PLT 1, is desirable that not only the components near the peak wavelength of the fluorescent spectrum, but also the band components near the edge portion can be efficiently detected. Further, in the above conventional configuration, since it limits the acquired fluorescence wavelength peak, if the fluorescence peak wavelength is slightly off, a remarkable drop in the efficiency of acquisition of fluorescence occurs, or a change of the optical coupler becomes necessary for the different types of fluorescent reagents.

An object of the present invention is to efficiently obtain an optical signal over a broad bandwidth using WDM-type optical couplers.

Solutions to Problems

The optical coupler device of the present invention includes a first WDM-type optical coupler and a second WDM-type optical coupler. The first WDM-type optical coupler has a first port, second port, and a fourth port that is positioned as a cross port when regarding the first port as an input end and is positioned as a straight port when regarding the second port as an input end. The second WDM-type optical coupler has a fifth port, sixth port, a seventh port that is positioned as a straight port when regarding the fifth port as an input end and positioned as a cross port when regarding the sixth port as an input end, and an eighth port that is positioned as a cross port when regarding the fifth port as an input end and positioned as a straight port when regarding the sixth port as an input end. The fourth port of the first WDM-type optical coupler and the fifth port of the second WDM-type optical coupler are optically coupled, and the second port of the first WDM-type optical coupler and the eighth port of the second WDM-type optical coupler are also optically coupled.

Preferably, the first WDM-type optical coupler and the second WDM-type optical coupler have transmittance characteristics where light with a first peak wavelength enters the first port and passes through the fourth and fifth ports before being emitted from the seventh port, while light that enters the seventh port has a second peak wavelength, which is longer than the first peak wavelength, and is emitted from the sixth port either directly or after passing through each of the fifth, fourth, second, and eighth ports.

For example, a period of transmittance between straight ports and between cross ports of the first WDM-type optical coupler is preferably 2 times the period of transmittance between straight ports and between cross ports of the second WDM-type optical coupler. Preferably, under this condition, a transmittance between cross ports of the peak wavelength of the second WDM-type optical coupler substantially matches the second peak wavelength. Further, a transmittance between cross ports of the first WDM-type optical coupler is preferably 80% or more at the first peak wavelength, for example. Further, a transmittance between straight ports of the second WDM-type optical coupler preferably reaches a peak at the first peak wavelength together with the transmittance between cross ports of the first WDM-type optical coupler, then reaches a next peak together with the transmittance between straight ports of the first WDM-type optical coupler.

Further, for example, the first WDM-type optical coupler and the second WDM-type optical coupler have the same transmittance characteristics. In this condition, preferably peak wavelengths of the transmittances between cross ports of the first and second WDM-type optical couplers substantially match the second peak wavelength. Preferably, from 50% to less than 100% of the transmittances between straight ports of the first and second WDM-type optical couplers include the first peak wavelength.

Further, the first WDM-type optical coupler has a third port which is positioned as a straight port when regarding the first port as an input end and the third port as a terminal end with no connections.

The confocal observation system of the present invention is a confocal observation system that includes the above optical coupler device. The confocal observation system includes a light source that emits light having a first peak wavelength and a light detector, the first port of the first WDM-type optical coupler is optically coupled with the light source, the sixth port of the second WDM-type optical coupler is optically coupled with the light detector, the light source emits the light to the observed subject through the seventh port of the second WDM-type optical coupler, and the light detector obtains return light, which has a second peak wavelength that is longer than the first peak wavelength, from the observed subject through the seventh port of the second WDM-type optical coupler.

The confocal observation system is preferably provided with a scanning means for confocal observation by producing light having the first peak wavelength that passes through the seventh port of the second WDM-type optical coupler to scan the observed subject. For example, the light emitted from the light source is used as excitation light, and the light obtained from the observed subject is fluorescent light due to the excitation light.

The scan-type confocal endoscope of the present invention is provided with the above confocal observation system.

Advantageous Effects of the Invention

According to the present invention, a WDM-type optical coupler can be used to efficiently obtain an optical signal over a broader bandwidth.

DESCRIPTION OF EMBODIMENTS

Figure 1:
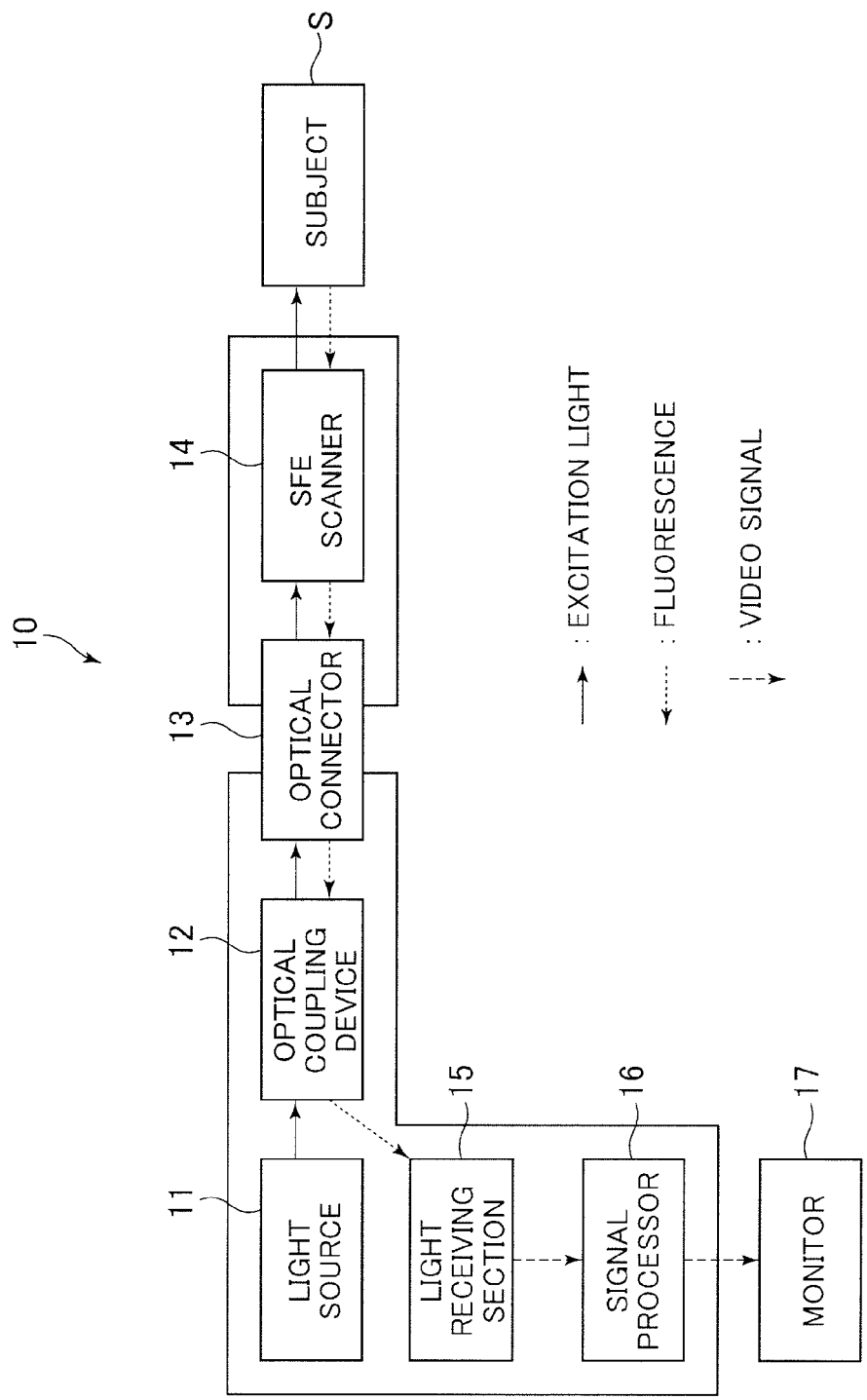
FIG. 1 is a block diagram which shows the configuration of a scan-type confocal endoscope which applies a confocal observation system of the present embodiment.

Below, embodiments of the present invention will be explained with reference to the drawings. FIG. 1 is a block diagram which shows the configuration of a confocal observation system which uses an optical coupler device of a first embodiment of the present invention.

In the present embodiment, the confocal observation system 10 is, for example, a scan-type confocal endoscope which introduces light from a light source 11 (for example excitation light) that passes through an optical coupler device 12, optical connector 13, and SFE scanner 14 through the tip of the endoscope to a subject S. The reflected light (for example fluorescence) from the subject S is detected through an SFE scanner 14, optical connector 13, and optical coupler device 12 at a photomultiplier tube (PMT) or other light-receiving section (light detector) 15, which has an excitation filter at its front stage. Signals from the light-receiving section 15 are sent to a signal processor 16. An image of the subject S, which is produced by the signal processor 16, is displayed on a monitor 17.

Figure 2:
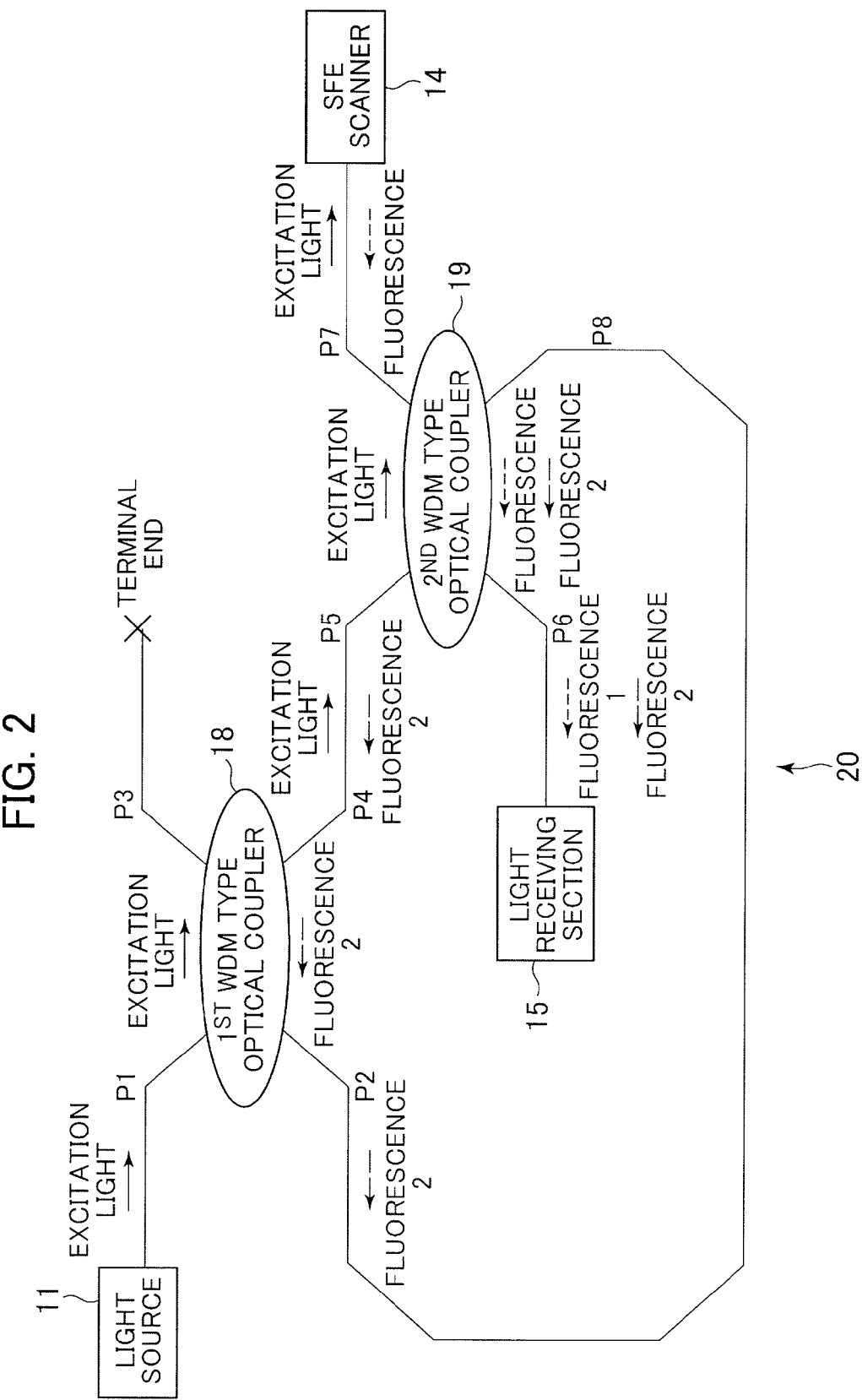
FIG. 2 is a block diagram which shows the configuration of an optical transmission system which is used in the confocal observation system of the present embodiment.

FIG. 2 is a block diagram which shows the configuration of an optical transmission system 20 of the present embodiment. The optical coupler device 12 of the present embodiment is configured by coupling a first WDM-type optical coupler 18 and a second WDM-type optical coupler 19. For the first and second WDM-type optical couplers 18 and 19, for example, a 2-input, 2-output (2×2) WDM-type optical coupler is used. Note that, in FIG. 2, the optical connector 13 is omitted.

The first WDM-type optical coupler 18 is provided with the first to fourth ports. The third port is positioned as a straight port when regarding the first port as the input end and is positioned as a cross port when regarding the second port as the input end. Further, the fourth port is positioned as a cross port when regarding the first port as the input end and is positioned as a straight port when regarding the second port as the input end.

Further, the second WDM-type optical coupler 19 is provided with fifth to eighth ports. The seventh port is positioned as a straight port when regarding the fifth port as the input end and is positioned as a cross port when regarding the sixth port as the input end. Further, the eighth port is positioned as a cross port when regarding the fifth port as the input end and is positioned as a straight port when regarding the sixth port as the input end.

The fourth port P4 of the first WDM-type optical coupler 18 is optically connected to the fifth port P5 of the second WDM-type optical coupler 19, while the second port P2 of the first WDM-type optical coupler 18 is optically connected to the eighth port P8 of the second WDM-type optical coupler 19. Further, in the present embodiment, the third port P3 of the first WDM-type optical coupler 18 is a terminal with no connections. The first and second WDM-type optical couplers 18 and 19, by being configured as above, function as a single optical coupler device 12 having a first port P1, sixth port P6, and seventh port P7 as input/output ports. The optical connection between the ports is formed by melt bonding, for example.

Further, in the present embodiment, the light source 11 is connected to the first port P1 of the optical coupler device 12, while the light-receiving section 15 and SFE scanner 14 are connected to the sixth port P6 and the seventh port P7, respectively. The scan-type confocal endoscope 10 of the present embodiment, for example, is used for fluorescent observation of a body. The light source 11 is a laser light source or LED light source that emits excitation light, which causes fluorescence of the observed subject or reagent.

The excitation light from the light source 11 is input through the first port P1 of the optical coupler device 12 and supplied through the seventh port P7 to the SFE scanner 14. The excitation light supplied to the SFE scanner 14 passes through the scanning fiber (not shown) and is emitted from the front end of the inserted part of the endoscope toward the observed subject, for example, to which a reagent has been applied. The fluorescence, which is caused by the excitation light, is emitted from the surface of the observed subject, passes through the scanning fiber of the SFE scanner 14, is input through the seventh port P7 to the optical coupler device 12, then exits through the sixth port P6 to the light-receiving section 15. The excitation light is laser light near 480 nm, for example. The light which is obtained from the observed subject is fluorescence of the 500 to 600 nm band, for example, which has a peak at 515 nm due to the excitation light.

Figure 9:
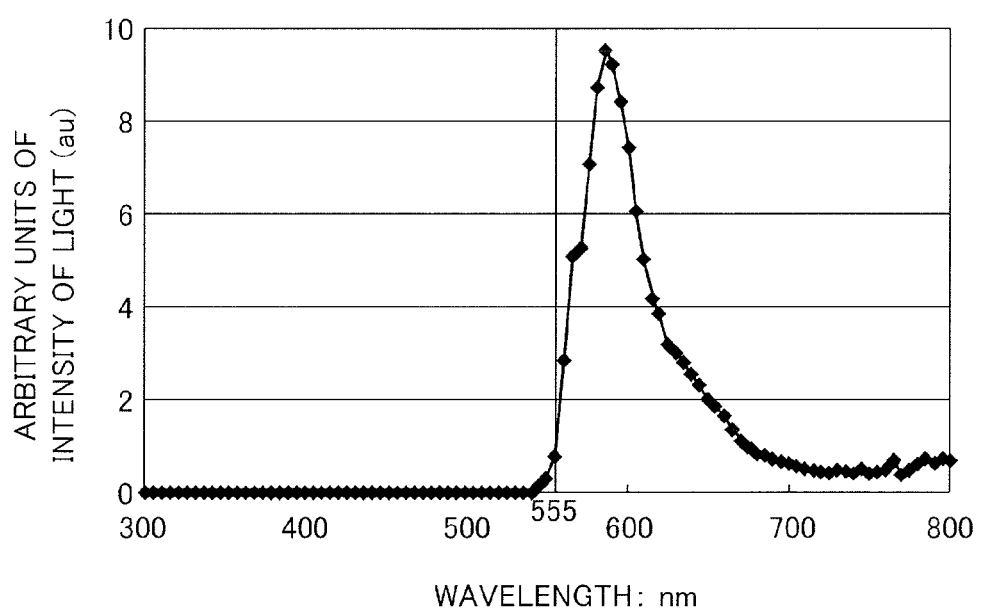
FIG. 9 is a graph which illustrates the spectral distribution of fluorescence of an observed subject with respect to 555 nm laser light.

Further, the excitation light may be laser light near 555 nm and the light which is obtained from the observed subject is fluorescent light in the 540 to 650 nm (700 nm) band, for example, with a peak at 585 nm due to excitation light. FIG. 9 shows the spectral distribution for the above-mentioned case (corresponding to the fluorescence of Rhodamine B). Note that in FIG. 9, the abscissa indicates the wavelength (nm), while the ordinate indicates an arbitrary unit (au) of the intensity of light.

The scanning fiber of the SFE scanner 14 comprises a single optical fiber, for example. A scanning mechanism (not shown), which uses a piezoelectric device, etc., is provided near the front end of the scanning fiber. The distal end of the scanning fiber is bent up, down, right, and left by a scanning mechanism while emitting excitation light, and receives the fluorescence of the return light that is focused at its tip end, thereby the observed subject is scanned two-dimensionally. The obtained fluorescence is detected by the light-receiving section 15 and processed later by the signal processing unit 16. Due to this, a 2D image of the observed subject is obtained. Note that, at the front stage of the light-receiving section 15, an excitation filter is arranged. The excitation filter effectively removes the components of excitation light that produce noise in the light-receiving section 15.

Next, referring to FIG. 3 and FIG. 4, the transmittance characteristics, actions and effects of the optical coupler device 12 of the first embodiment will be explained. Note that the first and second WDM-type optical couplers 18 and 19 used in the first embodiment have the same transmittance and branching ratio characteristics.

Figure 3:
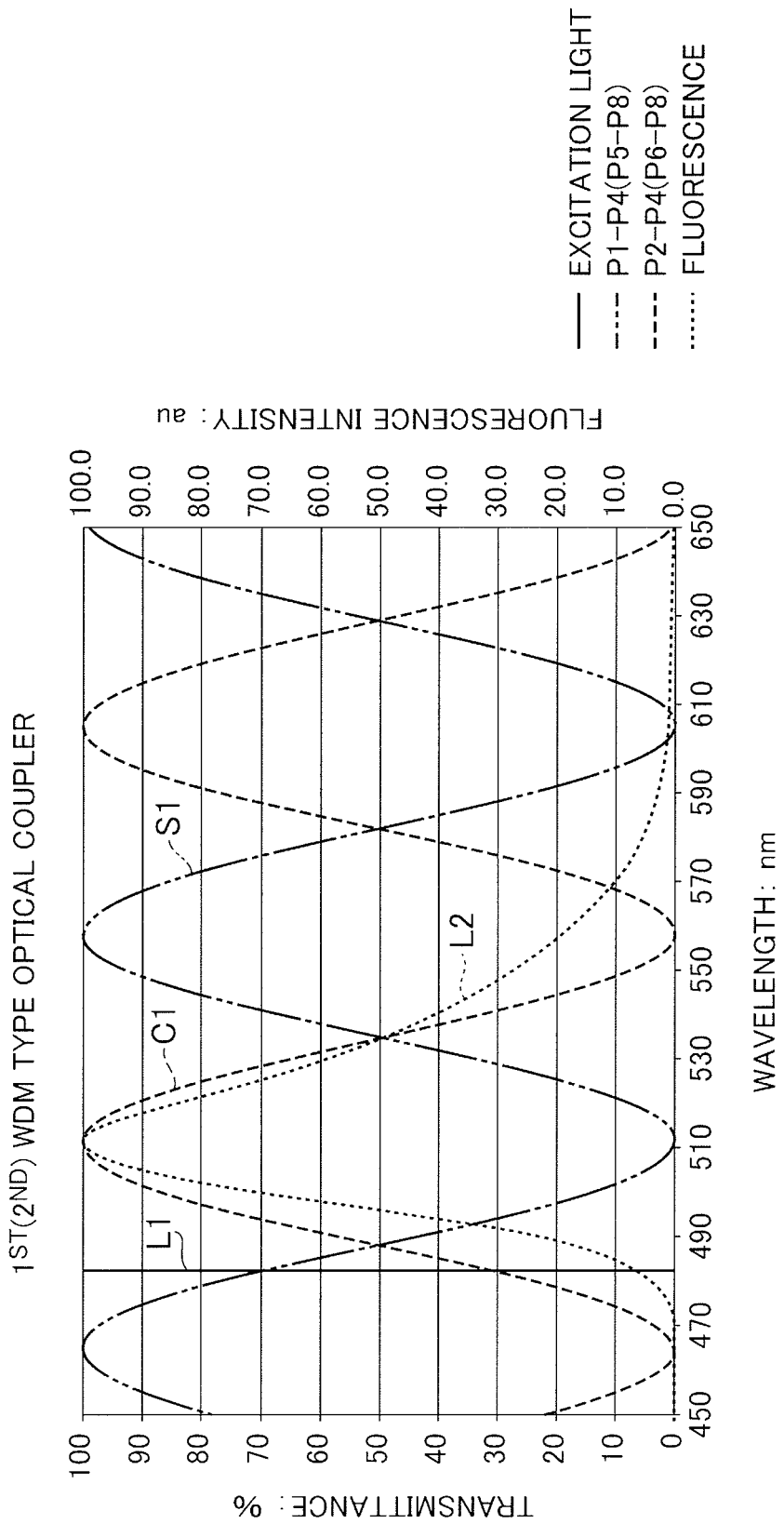
FIG. 3 is a graph which shows the transmittance characteristics of first and second WDM-type optical couplers, which form an optical coupler device of a first embodiment, and the spectral distributions of the excitation light and fluorescence.

FIG. 3 shows the transmittance characteristics of either of the first WDM-type optical coupler 18 or second WDM-type optical coupler 19, which are used in the first embodiment and have the same transmittance characteristics. Further, FIG. 3 shows the spectral distributions of the excitation light and fluorescence in the present embodiment. Note that in the graph of FIG. 3, the abscissa indicates the wavelength of light (nm), the left ordinate indicates the transmittance of light (%), and the right ordinate indicates an arbitrary unit (au) of the intensity of light.

In FIG. 3, the curve S1 shows the transmittances (%) between the straight ports of the first WDM-type optical coupler 18 and the second WDM-type optical coupler 19, while the curve C1 shows the transmittances (%) between the cross ports. The line L1 is the spectrum of the excitation light from the light source 11, which is input to the optical coupler device 12. The peak value is shown as 100(au). Further, the curve L2 is the spectrum of the fluorescence, which is input to the optical coupler device 12. The peak value is shown as 100(au).

The transmittances S1 and C1 exhibit complementary sine wave shapes with sums of 100%. One is offset 180° out of phase from the other. The transmittance characteristics of the first and second WDM-type optical couplers 18 and 19 of the present embodiment are set as follows: For the spectral distribution L2 of the fluorescence, the peak wavelength of the transmittance C1 between cross ports is set so as to substantially match the peak wavelength of the spectral distribution L2, while for the spectrum L1 of the excitation light, the band of 50% to less than 100% of the transmittance S1 between the straight ports is set so as to include the spectrum L1 (peak wavelength of excitation light). It is preferable that the transmittance S1 between straight ports is 50% with respect to the peak wavelength L1 of the excitation light.

Figure 4:
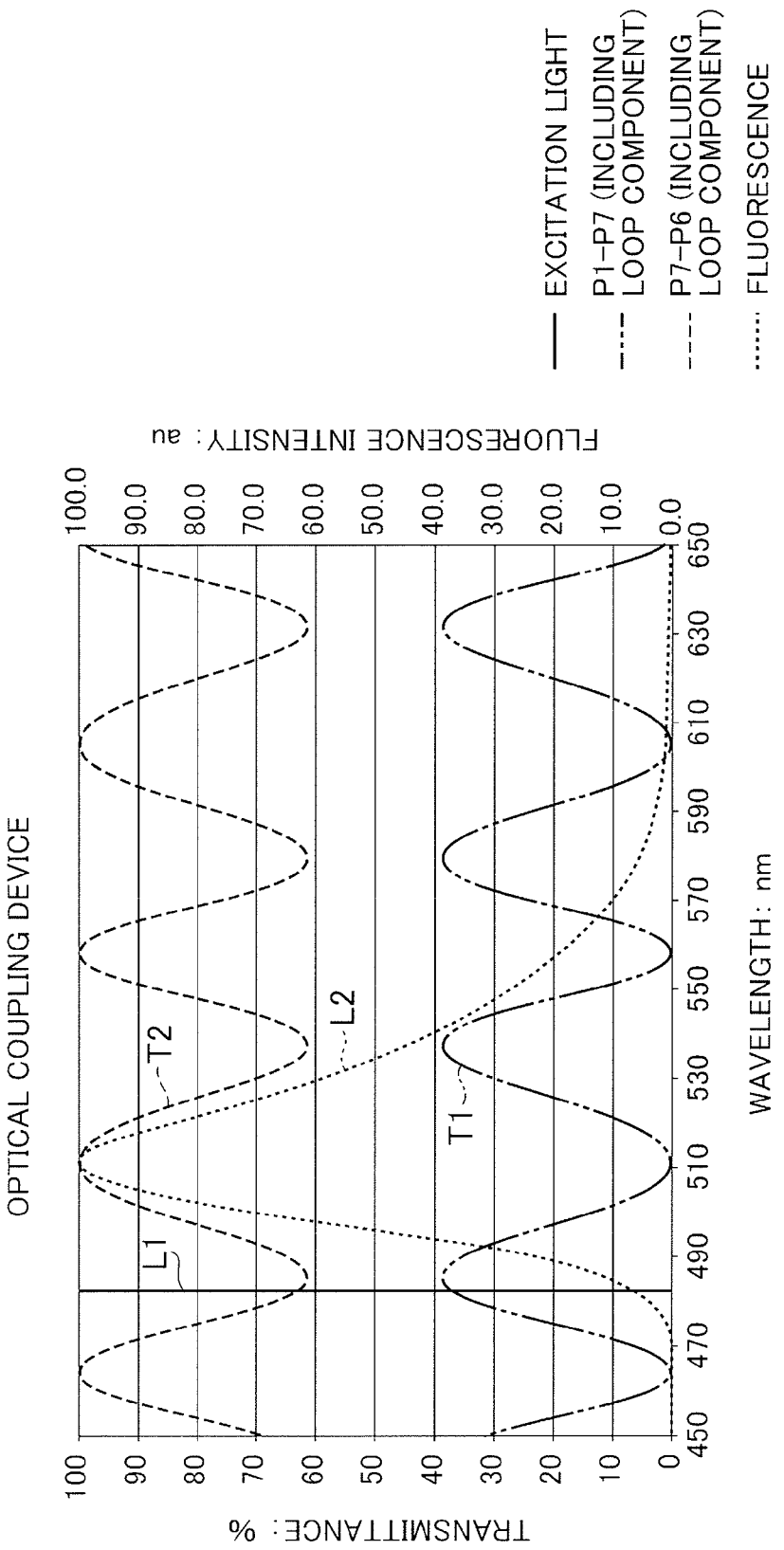
FIG. 4 is a graph which shows the transmittance between the first port and seventh port and the transmittance between the seventh port and sixth port in the optical coupler device of the first embodiment, and the spectral distributions of the excitation light and fluorescence.

FIG. 4 shows the transmittance characteristics of light from the first port P1 to the seventh port P7 (P1-P7) and the transmittance characteristics of light from the seventh port P7 to the sixth port P6 (P7-P6) of the optical coupler device 12, which comprises the first WDM-type optical coupler 18 and the second WDM-type optical coupler 19 coupled together. The abscissa indicates the wavelength of the light (nm), while the left ordinate indicates the transmittance of the light (%). Further, in the same way as FIG. 3, FIG. 4 shows the spectral distributions L1 and L2 of the excitation light and fluorescence so that the right ordinate shows arbitrary units (au) of the light intensity.

In the present embodiment, the second port P2 is optically connected to the eighth port P8 to form a loop, so that the light that is input from the fifth port P5 to the second WDM-type optical coupler 19 is further branched to the eighth port P8 and again input to the first WDM-type optical coupler 18 through the second port P2. Further, the light that is input from the seventh port P7 to the second WDM-type optical coupler 19 is further branched to the fifth port P5 and again input to the second WDM-type optical coupler 19 through the second port P2 of the first WDM-type optical coupler 18 and the eighth port P8 of the second WDM-type optical coupler 19. Due to this, the transmittance between the ports P1 to P7 of the optical coupler device 12 is represented by the curve T1, while the transmittance between the ports P7 to P6 is represented by the curve T2.

That is, when using the optical coupler device 12 of the present embodiment, the transmittance with respect to the excitation light, which is guided through the first port P1 to the seventh port P7 to the SFE scanner 14, stabilizes at about 40%. If taking note of the fluorescence, which is input from the seventh port P7, the fluorescence component in the band near the peak (fluorescence 1) is output from the seventh port P7 directly to the sixth port P6. Further, most of the fluorescence component that is branched to the fifth port P5 (fluorescence 2) is again input to the second WDM-type optical coupler 19 via a loop between the second port P2 and eighth port P8, and then output through the sixth port P6.

Accordingly, as shown in FIG. 3, at the light-receiving section 15, it is not only possible to obtain the light in the peak wavelength band of the fluorescence components almost without loss, but also possible to obtain a broader band than when using a single WDM-type optical coupler.

As explained above, according to the first embodiment of the present invention, fluorescence 2, which could not be obtained in prior art, can be efficiently detected, so that an optical signal over a broader bandwidth can be efficiently obtained by using WDM-type optical couplers. Further, according to the present embodiment, even if the wavelength of the fluorescent peak becomes somewhat off, a drop in the acquisition efficiency of the fluorescence can be prevented, so it becomes possible to handle a broad range of fluorescent reagents.

Next, referring to FIGS. 5 to 8, an optical transmission system of a second embodiment of the present invention will be explained. The optical transmission system of the second embodiment is similar to the first embodiment except that WDM-type optical couplers with different transmittance characteristics from one another are used for the first WDM-type optical coupler and the second WDM-type optical coupler of the optical coupler device 12. Therefore, parts of the configuration that are similar to the first embodiment are assigned the same reference notations and their explanations will be omitted.

Figure 5:
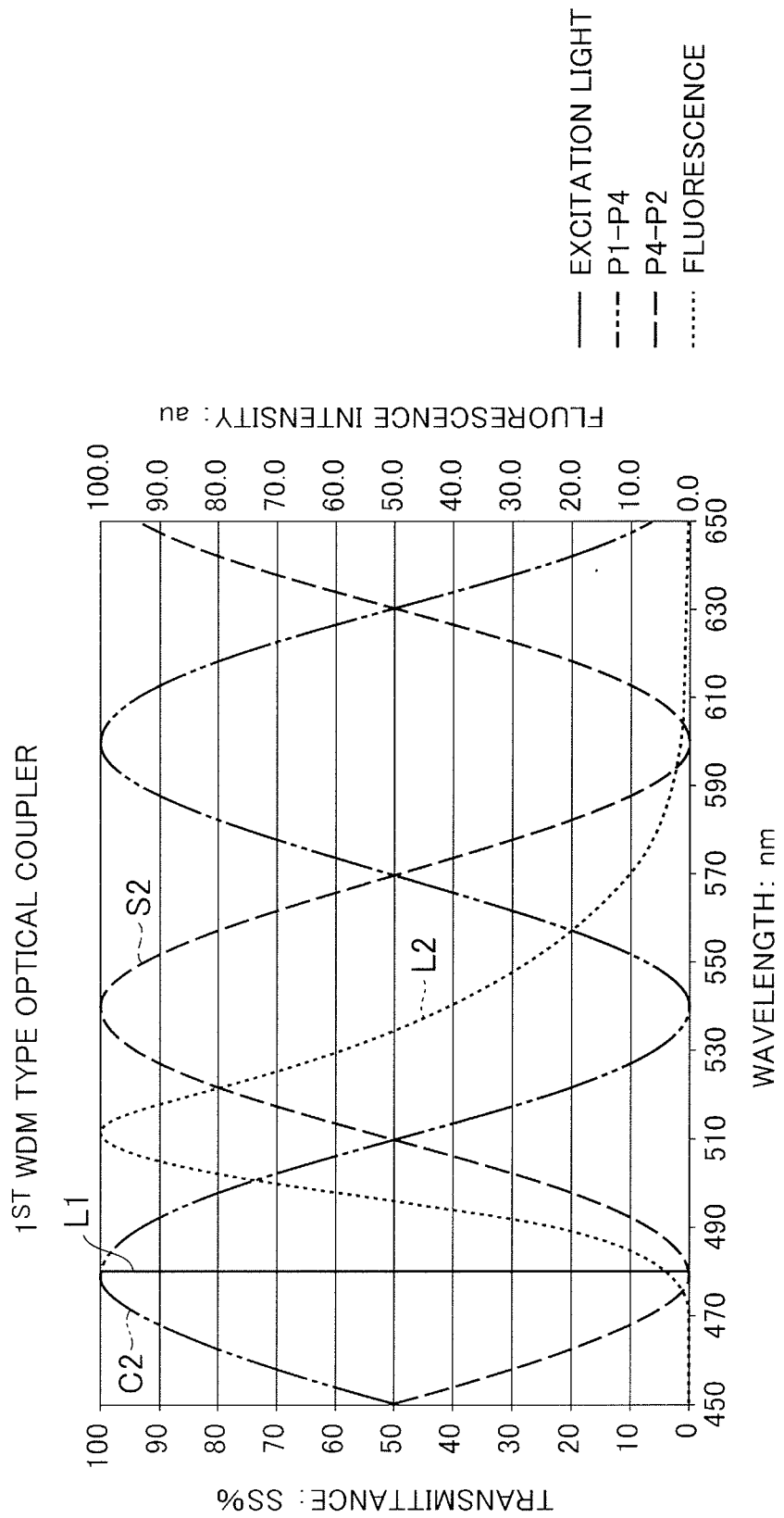
FIG. 5 is a graph which shows the transmittance characteristic of the first WDM-type optical coupler, which forms an optical coupler device of a second embodiment, and the spectral distributions of the excitation light and fluorescence.
Figure 6:
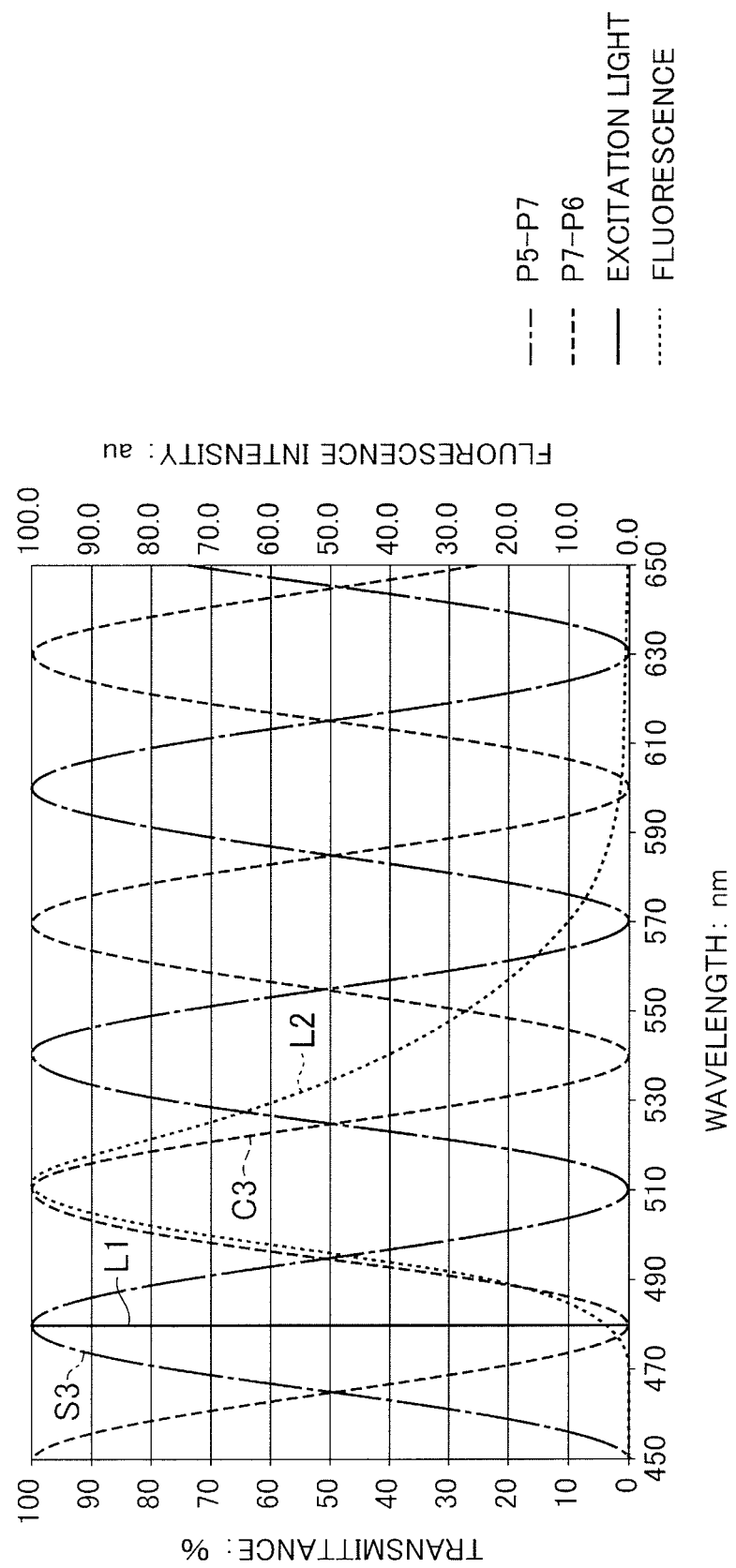
FIG. 6 is a graph which shows the transmittance characteristic of the second WDM-type optical coupler, which forms an optical coupler device of a second embodiment, and the spectral distributions of the excitation light and fluorescence.
Figure 7:
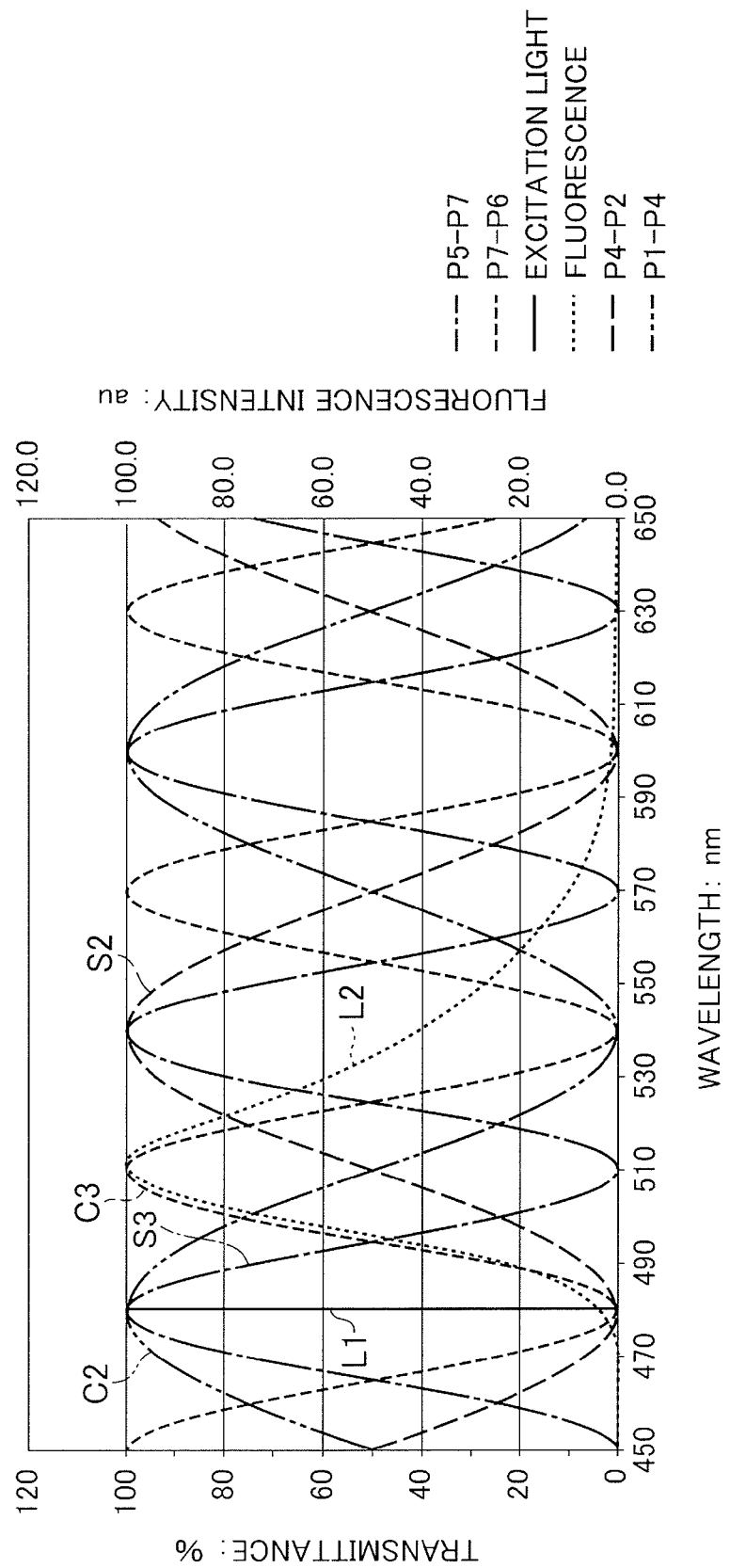
FIG. 7 is a graph which shows the relationship between the transmittances of the first and second WDM-type optical couplers in the second embodiment.

FIG. 5 and FIG. 6 are graphs which show the transmittance characteristics of the first WDM-type optical coupler 18 and the second WDM-type optical coupler 19 in the second embodiment, and the spectral distributions L1 and L2 of the excitation light and fluorescence. The curve S2 of FIG. 5 shows the transmittance (%) between the straight ports (P1-P3, P4-P2) of the first WDM-type optical coupler 18, the curve C2 shows the transmittance (%) between the cross ports (P1-P4) of the first WDM-type optical coupler 18, the curve S3 of FIG. 6 shows the transmittance (%) between the straight ports (P5-P7, P8-P6) of the second WDM-type optical coupler 19, and the curve C3 shows the transmittance (%) between the cross ports (P5-P8, P7-P6) of the second WDM-type optical coupler 19. Further, FIG. 7 shows the curves of FIG. 5 and FIG. 6 in the same graph. Note that the physical quantities for the axes in the different graphs are similar to those of FIGS. 3 and 4.

As shown in FIG. 5, in the first WDM-type optical coupler 18 of the second embodiment, to have as much as possible of the excitation light, which is input from the first port P1, introduced into the fourth port P4, the transmittance C2 is selected as the transmittance between the cross ports (P1-P4). Further, in the first WDM-type optical coupler 18 of the second embodiment, the transmittance S2 between the straight ports (P4-P2) is selected to introduce as much (without loss) as possible of the fluorescence 2, which is input from the fourth port P4, to the second port P2. For example, the branching rate of the excitation light between the ports P1-P3 is 0% to 20% (that is, the branching rate between the ports P1-P4 is 100% to 80%). Note that, in this condition, not much at all of the reflected component of the excitation light enters the second port P2 even if it is input from the fourth port P4.

On the other hand, as shown in FIG. 6, in the second WDM-type optical coupler 19 of the second embodiment, to have as much as possible of the excitation light, which is input from the fifth port P5, introduced into the seventh port P7, the transmittance S3 is selected as the transmittance between the straight ports (P5-P7). Further, in the second WDM-type optical coupler 19 of the second embodiment, the transmittance C3 between the cross ports (P7-P6) is selected so as to introduce the fluorescence 1, which represents the band component near the peak of the fluorescence that is input from the SFE scanner 14 to the seventh port P7, to the sixth port P6 without loss. For example, the branching rate of the excitation light between the ports P5-P7 is 100% to 80% (that is, the branching rate between the ports P5-P8 is 0% to 20%). Further, the transmittance C3 is selected so that the peak of the fluorescence, which is input from the seventh port P7, will substantially match the peak of the transmittance C3 between the cross ports (P7-P6) of the second WDM-type optical coupler 19. Note that, in this condition, not much at all of the reflected component of the excitation light enters the sixth port P6, even if it is input from the seventh port P7.

Further, as shown in FIG. 5 and FIG. 6, in the second embodiment, for example, the periods of the transmittances S2 and C2, which are between the straight ports and between the cross ports of the first WDM-type optical coupler 18, are set to values about two times or more (for example, integers of 2 or more) than the periods of the transmittances S3 and C3, which are between the straight ports and between the cross ports of the second WDM-type optical coupler 19. In the present embodiment, 2 times are envisioned.

Figure 8:
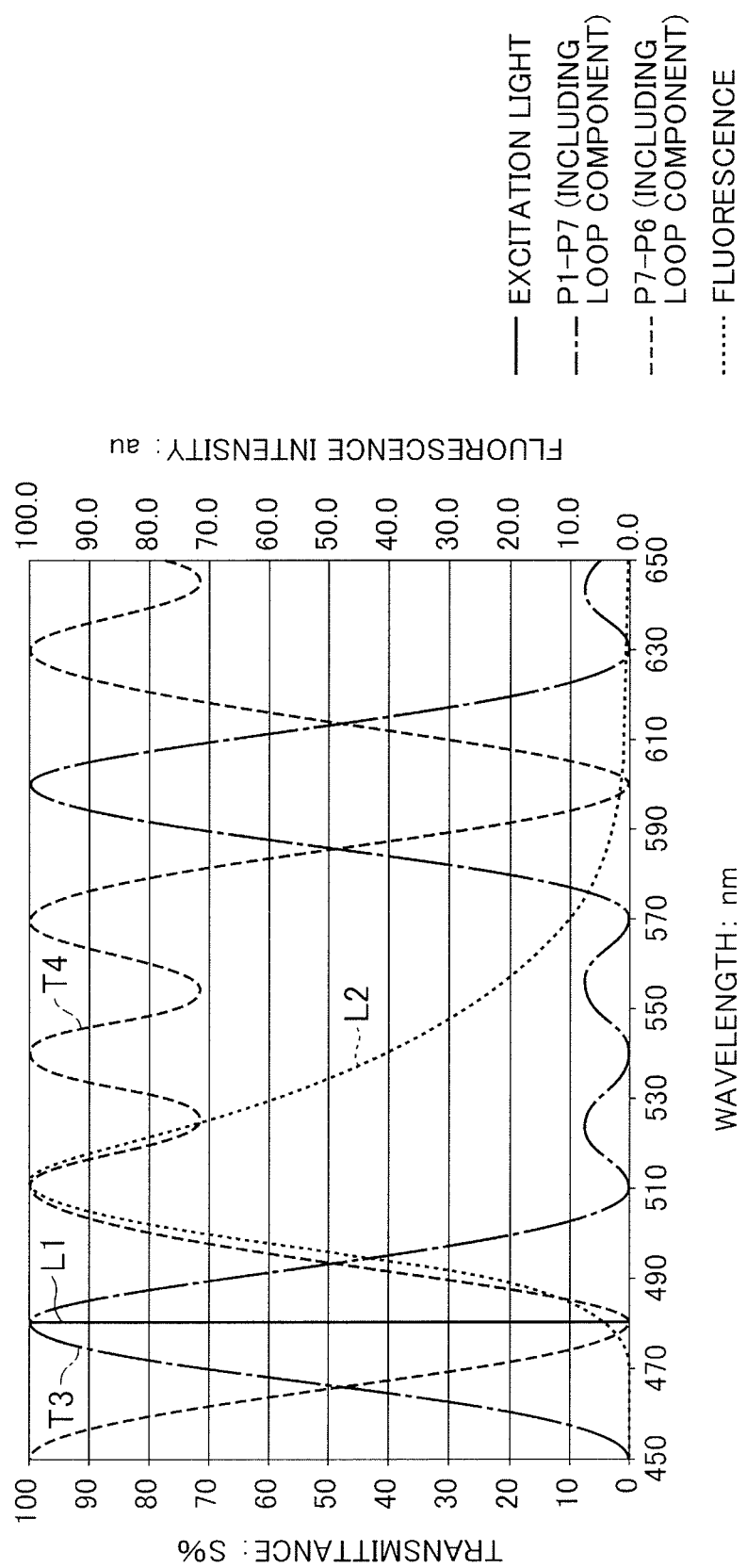
FIG. 8 is a graph which shows the relationship of the transmittance between the first port and seventh port, the transmittance between the seventh port and sixth port, and the spectral distributions of the excitation light and fluorescence in an optical coupler device of the second embodiment.

FIG. 8 shows the transmittance characteristics of light from the first port P1 to seventh port P7 (P1-P7) and the transmittance characteristic of light from the seventh port P7 to the sixth port P6 (P7-P6) of the optical coupler device 12 of the second embodiment. The abscissa shows the wavelength of the light (nm), while the left ordinate shows the transmittance of the light (%). Further, in the same way as FIGS. 5 to 7, FIG. 8 shows the spectral distributions L1 and L2 of the excitation light and fluorescence, while the right ordinate shows the arbitrary units (au) of the intensity of light.

When the relationship of the transmittances of the optical couplers 18 and 19 are set at the above conditions, the transmittances between the ports have the relationship shown in FIG. 7. Specifically, the transmittance C2 between the cross ports of the first WDM-type optical coupler 18 and the transmittance S3 between the straight ports of the second WDM-type optical coupler 19 both peak near the 480 nm peak wavelength of excitation light. Furthermore, the peak of the transmittance S3, which is next to the peak at about 480 nm, appears around a wavelength range that is the same as the peak of the straight port transmittance S2 of the first WDM-type optical coupler 18 (in the present embodiment, around 540 nm).

Therefore, as shown in FIG. 8, in the second embodiment, the transmittance between the ports P1-P7 of the optical coupler device 12 is represented by the curve T3, while the transmittance between the ports P7-P6 is represented by the curve T4. That is, in the second embodiment, the transmittance T3 between the ports P1-P7 exhibits a narrow-band transmittance distribution with a high transmittance only near the peak wavelength of the excitation light. Further, as explained above, by substantially matching the peak of the transmittance S3 and the peak of the transmittance S2 in a predetermined wavelength band, the transmittance T4 between the ports P7-P6 exhibits a transmittance distribution with a high transmittance over a broad band that includes the overall spectrum of fluorescent light.

Accordingly, in the second embodiment of the present invention, it is also possible to obtain similar effects as the first embodiment and possible to configure an optical coupler which has a transmittance distribution over a relatively narrower band for the irradiated light and a transmittance distribution over a relatively broader band for the return light.

In the present embodiment a laser beam, which has a line spectrum, was used as an example for the irradiated light (excitation light), but the present embodiment can also be applied with the use of LEDs, etc., which produce a narrow band light with a continuous spectral distribution, as an irradiated light (excitation light) source. Further, in the present embodiment, as the return light, fluorescence was used as an example, but the invention is not limited to fluorescence as the return light. Namely, the invention can also be applied to the case when irradiating the light with the peak wavelength $\lambda 1$ and detecting the reflected light with the peak wavelength $\lambda 2$ ($\neq \lambda 1$) as the return light. If selecting the transmittances between the straight ports and cross ports of two WDM-type optical couplers on the basis of the peak wavelengths λ1 and λ2 of the irradiated light and return light, as in the present embodiment, it becomes possible to efficiently obtain the return light over a broad wavelength band.

Note that, the optical transmission system of the present invention may also be used for a microscope or other application in addition to an endoscope. Further, in a scan-type confocal endoscope, the fiber is moved to scan an observed subject, but when used for a microscope etc., the sample side may also be moved for scanning.

In the present embodiment, a 2×2 input/output WDM-type optical coupler was used, however, a 2-input, 1-output coupler may also be used as a first WDM-type optical coupler. Further, the number of input/output ports is not limited to the number of the present embodiment.

REFERENCE SIGNS LIST 10 confocal observation system
11 light source
12 optical coupler device
14 SFE scanner
15 light-receiving section (light detector)
18 first WDM-type optical coupler
19 second WDM-type optical coupler

The invention claimed is:

1. An optical coupler device comprising:
a first WDM-type optical coupler having a first port, second port and a fourth port that is positioned as a cross port when regarding said first port as an input end and positioned as a straight port when regarding said second port as an input end; and
a second WDM-type optical coupler having a fifth port, sixth port, a seventh port that is positioned as a straight port when regarding said fifth port as an input end and positioned as a cross port when regarding said sixth port as an input end, and an eighth port that is positioned as a cross port when regarding said fifth port as an input end and positioned as a straight port when regarding said sixth port as an input end;
said fourth port of said first WDM-type optical coupler and said fifth port of said second WDM-type optical coupler being optically coupled and said second port of said first WDM-type optical coupler and said eighth port of said second WDM-type optical coupler being optically coupled.

2. The optical coupler device according to claim 1, wherein said first WDM-type optical coupler and said second WDM-type optical coupler have transmittance characteristics where
light having a first peak wavelength that enters said first port is emitted from said seventh port through said fourth and fifth ports; and
light having a second peak wavelength longer than the first peak wavelength that enters from said seventh port is directly emitted from said sixth port or is emitted from said sixth port after passing through each of said fifth, fourth, second and eighth ports.

3. The optical coupler device according to claim 2, wherein a period of transmittance between straight ports and between cross ports of said first WDM-type optical coupler is 2 times the period of transmittance between straight ports and between cross ports of said second WDM-type optical coupler.

4. The optical coupler device according to claim 3, wherein a peak wavelength of a transmittance between cross ports of said second WDM-type optical coupler substantially matches said second peak wavelength.

5. The optical coupler according to claim 3, wherein a transmittance between cross ports of said first WDM-type optical coupler for said first peak wavelength is 80% or more.

6. The optical coupler device according to claim 2, wherein said first WDM-type optical coupler and said second WDM-type optical coupler have the same transmittance characteristics.

7. The optical coupler device according to claim 6, wherein the regions of 50% to less than 100% of the transmittances between straight ports of said first and second WDM-type optical couplers include said first peak wavelength.

8. The optical coupler device according to claim 3, wherein a transmittance between straight ports of said second WDM-type optical coupler reaches a peak at said first peak wavelength together with the transmittance between cross ports of said first WDM-type optical coupler, then reaches a next peak together with the transmittance between straight ports of said first WDM-type optical coupler.

9. The optical coupler device according to claim 6, wherein peak wavelengths of the transmittances between cross ports of said first and second WDM-type optical couplers substantially match said second peak wavelength.

10. The optical coupler device according to claim 1, wherein said first WDM-type optical coupler comprises a third port which is positioned as a straight port when regarding said first port as an input end and where said third port is terminated.

11. A confocal observation system comprising said optical coupler device according to claim 1, wherein said confocal observation system comprising:
a light source that emits light having a first peak wavelength and a light detector;
said first port of said first WDM-type optical coupler is optically coupled with said light source;
said sixth port of said second WDM-type optical coupler is optically coupled with said light detector;
said light source emits the light to an observed subject through said seventh port of said second WDM-type optical coupler; and
said light detector obtains return light from the observed subject that has a second peak wavelength which is longer than said first peak wavelength through said seventh port of said second WDM-type optical coupler.

12. The confocal observation system according to claim 11, comprising a scanning means for confocal observation by scanning said observed subject with light having said first peak wavelength which has passed through said seventh port of said second WDM-type optical coupler.

13. The confocal observation system according to claim 11, wherein the light which is emitted from said light source is used as excitation light and the light which is obtained from said observed subject is fluorescent due to said excitation light.

14. A scan-type confocal endoscope comprising said confocal observation system in claim 11.

* * * * *